United States Patent [19]
Viitasalo

[11] Patent Number: 6,074,064
[45] Date of Patent: *Jun. 13, 2000

[54] APPARATUS FOR MEASURING LIMITS OF A PERIPHERAL VISUAL FIELD

[76] Inventor: Veikko Viitasalo, FIN-71720 Kaarmelahti, Finland

[*] Notice: This patent issued on a continued prosecution application filed under 37 CFR 1.53(d), and is subject to the twenty year patent term provisions of 35 U.S.C. 154(a)(2).

[21] Appl. No.: 08/825,468

[22] Filed: Mar. 28, 1997

[51] Int. Cl.⁷ ........................................... A61B 3/02
[52] U.S. Cl. ............................... 351/237; 351/224
[58] Field of Search .................... 351/224, 226, 351/237, 239

[56] References Cited

U.S. PATENT DOCUMENTS

| | | | |
|---|---|---|---|
| 3,737,217 | 6/1973 | Haines et al. | 351/224 |
| 4,346,968 | 8/1982 | Melin et al. | 351/224 |
| 5,302,981 | 4/1994 | Wirtz | 351/224 |

FOREIGN PATENT DOCUMENTS

| | | |
|---|---|---|
| 2307809 | 8/1973 | Germany . |
| 2454387 | 5/1976 | Germany . |

OTHER PUBLICATIONS

Lyman C. Norden, O.D., "Reliability in perimetry," Journal of the American Optometric Association, Dec. 1989, pp. 880–890.

Harley, "Ophthalmic Examinations of Infants and Children", Pediatric Ophthalmology, Second Edition, 1983, p. 127.

*Primary Examiner*—Huy Mai
*Attorney, Agent, or Firm*—Pillsbury Madison & Sutro LLP

[57] ABSTRACT

An apparatus for measuring the limits of a visual peripheral field includes a gaze-fixing mirror containing a dot for fixing the gaze of an examinee, a backing to which the mirror is fastened, and a base to which the backing is joined. The base forms a storage space for a measuring tool and at least one target object. The mirror, the backing and the base are collapsible and easily transportable by a single hand. The system replaces widely-known finger perimetry methods now in general use and positions the examiner behind the examinee. The examiner monitors the examinee's gaze with the help of the mirror while introducing target objects into the visual field of the examinee. The examinee indicates awareness of the target objects so that the limits of the examinee's visual peripheral field can be noted and recorded.

11 Claims, 2 Drawing Sheets

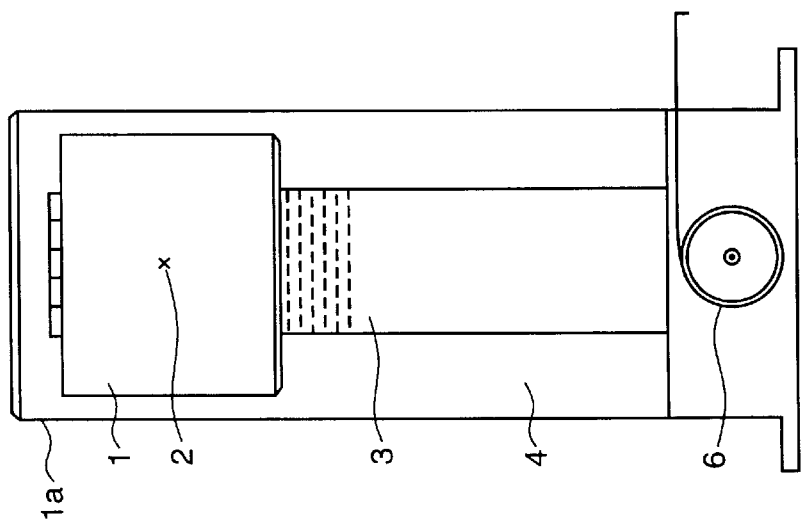
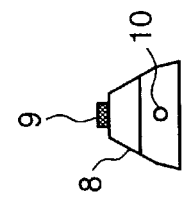
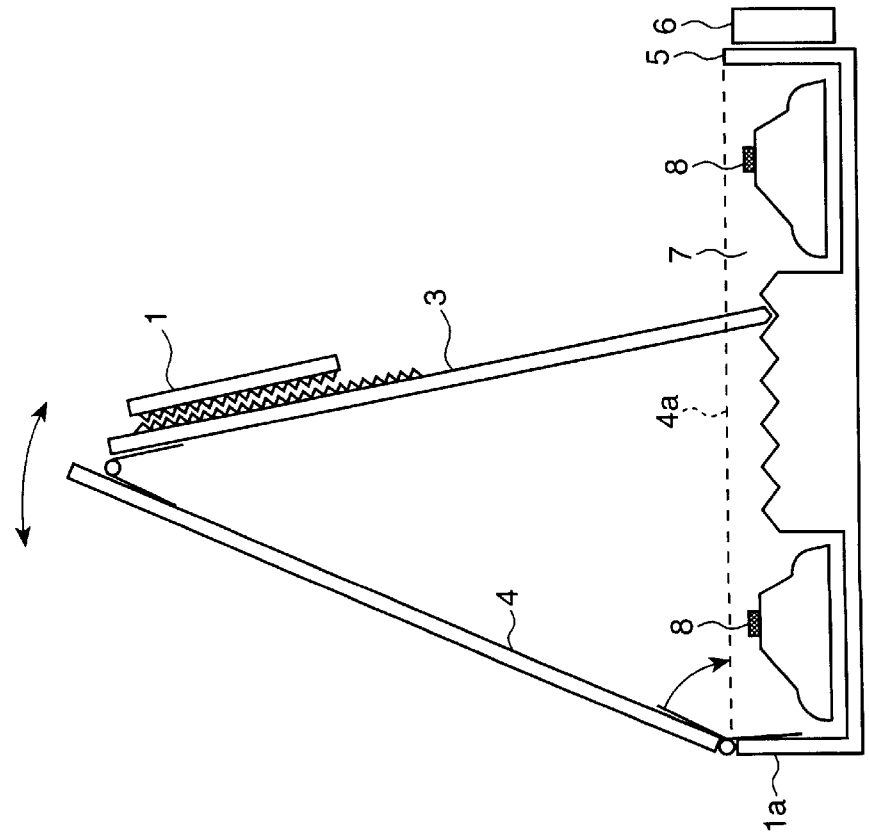

APPARATUS FOR MEASURING LIMITS OF A PERIPHERAL VISUAL FIELD

BACKGROUND OF THE INVENTION

1. Field of the Invention

The present invention relates to equipment for assessing the functional peripheral visual field.

2. Description of the Related Art

Visual field testing belongs to the subspecialty of ophthalmology. However, it is very often performed at the primary health care level too, for example, as part of the medical examination required for obtaining a driver's license. The importance of visual field testing is emphasized by the Jul. 1, 1996, EU directive concerning health standards for drivers, which mandates "a field of vision of at least 120 degrees in the horizontal plane" as part of the minimum visual requirements for safe driving.

Many types of technical equipment have been developed for ophthalmologists working in hospitals and outpatient clinics. Nowadays the majority are computerized. The relevant literature (R. D. Harley, Pediatric Ophthalmology, $2^{nd}$ edition, p. 127, FIG. 4–32) contains only one mention of a method in which the examiner stands behind the examinee. All other methods position the examiner in front of the examinee or to the side. Perimetry examinations focus mainly on the diagnosis of diseases and on the determination of the central visual field during monocular examination. Functional binocular visual field testing has not yet been accepted into general practice, nor has its importance been emphasized. Furthermore, binocular examination has involved very complicated methods not easily utilized at the primary care level.

At this moment all physicians can choose from a variety of finger perimetry techniques for visual field testing. In the traditional static finger confrontation method, which is shown FIG. 1, the doctor D sits facing the examinee E at a distance of one meter and introduces fingers into the examinee's visual field from the periphery with the arms outstretched to the sides. While maintaining focus on the tip of the doctor's nose, the examinee tells how many fingers the doctor is holding up on either hand. In the kinetic confrontation method, the doctor and examinee are positioned as above, with the examinee again gazing at the tip of the doctor's nose. The doctor moves his hands from the periphery towards the center field, and the examinee signals when he/she can see the moving fingers. Results are compared with the doctor's own perception, and the techniques are poorly standardized.

This examiner has encountered many problems assessing visual fields during his 15 years of general practice, and many of his colleagues have expressed similar dissatisfaction with finger perimetry techniques. First, visual field defects are rare among people younger than 60 years of age, and those defects induced by glaucoma in older people are very difficult to verify by finger perimetry, so there are "never" positive findings. Also, because assessment of the visual fields by finger perimetry depends on cooperation between the doctor and the examinee as well as on the method, the examiner is plagued by uncertainty. This uncertainty arises because: (a) the examinee can see the position of the examiner's arms throughout the examination, (b) the extent of the field tested is limited by the examiner's armspan, (c) results can be recorded only as "normal" or "abnormal", not in degrees (as required by the EU directive on drivers' health standards), (d) the "wiggling fingers and moving arms" method appears rather comical, and does not increase the examinees' motivation or understanding, and (e) size differences between the examiner and examinee lead to further difficulties (for example, in the examination of children).

SUMMARY OF THE INVENTION

It is an object of the present invention to provide an apparatus for assessing the functional peripheral visual field where this apparatus is designed for visual field screening at the primary care level. It is also an object of the invention to provide an apparatus which allows perimetry measurements by monocular or binocular techniques with the examiner positioned behind the examinee.

The objects of the invention are attained by an apparatus comprising a gaze-fixing mirror containing a dot for fixing the gaze, where the mirror is fastened to a backing, where the backing is joined to a base, which forms a storage space for a measuring tool and at least one target object, and where the mirror, the backing and the base are easily transportable a by one hand and collapsible.

The invention described in this application is not intended to replace computerized equipment in diagnostics, but rather is designed for visual field screening at the primary care level by general practitioners, optometrists, nurses at well-baby and occupational health clinics, as well as ophthalmologists without computerized facilities. This invention allows perimetry measurements by monocular or binocular techniques with the examiner positioned behind the examinee, in direct contrast to the positioning in the traditional confrontation methods.

There is currently no method available at the primary care level by which the extent of the visual field can be assessed in degrees. This invention makes such examination possible. In addition, the numerical results it provides are easy to repeat and to compare with previous results by the same or different examiners.

Because this equipment is so simple, it will be affordable by examiners all over the world. It is also easy to transport, so that examinations can be made e.g. at the examinee's home.

BRIEF DESCRIPTION OF THE DRAWINGS

The invention is next presented with help of the attached drawings, in which

FIG. 2 shows a side view of an apparatus according to this invention,

FIG. 3 shows a detailed side view of a target,

FIG. 4 shows a front view of an apparatus illustrated in FIG. 2,

DETAILED DESCRIPTION OF THE PRESENTLY PREFERRED EMBODIMENT

Figure 6:
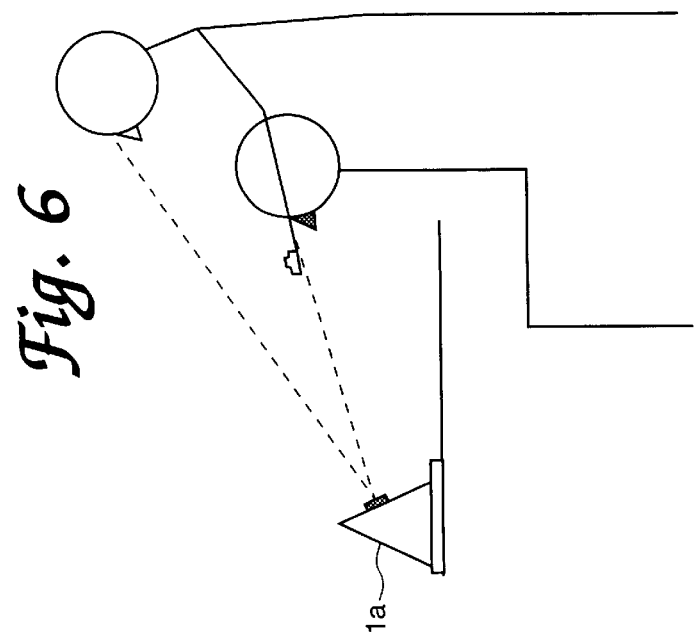
FIG. 6 shows the apparatus illustrated in FIG. 1 in use, viewed from the side.
Figure 1:
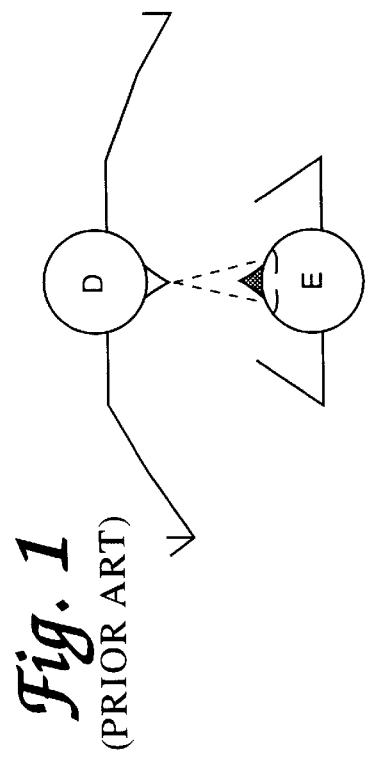
FIG. 1 shows a traditional finger perimetry.

A preferred embodiment of the present invention is shown in FIG 2. The heart of the invention is a small mirror for controlling the gaze of the examinee, the gaze-fixing mirror 1, containing a dot 2 for fixing the gaze situated at the center of the mirror. The examiner controls the gaze of the examinee by monitoring from a position behind him/her. Because of the mirror's small size, the examinee sees only a portion of the examiner's face in the mirror, not the examiner's arms. This feature is a major advantage of this invention, and so the diameter of the mirror is critical. The mirror is fastened to an A-shaped backing having a stand 3 and a back 4. At the front of the device the stand 3 supports the mirror and makes it possible to remove or change the mirror and to adjust its position up or down. This backing is joined onto a base 5 hinged in such a way that when the backing is folded down, the back 4 forms a cover for a storage space 7 in the base 5. A tool 6 for measuring or scaling degrees is attached to the base 5. The storage space 7 is large enough to contain for at least two target objects 8. Each target object includes a switch 9 to control a blinking light 10, as seen from FIG. 3. Small, car-shaped targets can be used to motivate even children to participate in the examination. Targets can be of different shapes and colors, so that the examinee does not know beforehand what kind of target is about to present itself. The light makes even more variations possible.

Figure 5:
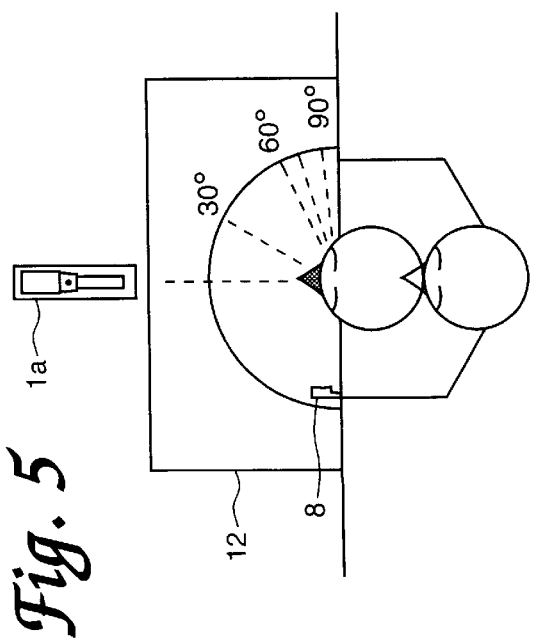
FIG. 5 shows the apparatus illustrated in FIG. 1 in use, viewed from above.

As illustrated in FIG. 5 using the measuring tool, a half circle with a radius of 30 cm is drawn onto a sheet of paper 12 on a table. A line drawn from the center straight forward to the perimeter is marked as zero degrees. The rest of the half circle is divided into ten-degree segments and labeled in increments up to 90 degrees, increasing in both directions away from the center zero-degree line. Alternatively, a re-usable plastic scaled, folding, removable plate joined to the equipment base can be used. Further information regarding the scaled plate will be provided in the manual.

The examinee is seated in front of the table with his/her gaze directed straight forward in the direction of the small mirror, which is placed opposite him/her on the zero-degree line. It is easy to position the plate/scaled paper so that the 90-degree line lies along the edge of the table and the examinee's face falls in the same vertical plane. The mirror is adjusted so that the examiner, standing behind the examinee, can see the examinee's eyes reflected in the mirror. The distance between the face of the examinee and the mirror is approximately the length of the examiner's forearm. Because the examinee is seated and the examiner is standing, the mirror must be adjusted so that the gazes of both coincide, as seen from FIG. 6. After this adjustment, the examiner introduces a target into the visual field of the examinee from one or both sides, as seen from FIG. 5, at the same time controlling the gaze of the examinee in the mirror. The target(s) is advanced ten degrees at a time, and the examinee signals when he/she notices it. This position in degrees is recorded as the peripheral limit of the visual field.

The above description only covers the assessment of the horizontal visual field, which is needed for obtaining a driver's license. However, the invention can also be used to measure the extent of the visual field in other directions and using different routines. For example, the target can be located first at the centre of the visual field, then moved to the periphery. The breadth of the blind spot can be measured monocularly by positioning the scaled plate 60 cm in front of the examinee's face and beginning the examination with the target in the blind spot, then moving it towards the periphery. Different coloured targets and backgrounds can be used to emphasize contrast. With the mirror fastened to a wall and using a bull's eye-type reference plate marked in ten-degree increments, the visual field can be measured in all directions using a flashing light target.

In addition to measuring visual fields, the device can also be used by school children during traffic education, as well as by driver's license applicants. It provides a comprehensible method for teaching the importance of the visual field. It can also be used to demonstrate the blind spot. Because vision also includes alertness and attention, people with these types of problems can use the device to train their visual capacity. The device can also be used in cognitive testing, as the visual field has become a topic of interest among researchers in the areas of dementia and cognition in general. The visual field is also important for military training and sport skills. By changing the targets and backgrounds, the device can be made into a stimulating toy to bring two people together in an exciting way.

Some pilot studies have been done using the device (not published). For instance, using medical students as subjects, black and yellow triangles were presented in an alternating sequence. When the test was repeated after one week, the results had improved. The test was also performed with 17 school children aged 9–11 years, and they found it exciting and easy.

As is well known, medicine is not mechanics, thus human aspects must be respected when new instruments are designed. Also, physicians do not accept a new instrument into practice Is if it is too complicated, even if the new instrument is better than the old one. Therefore, the equipment discussed above does not include more complicated systems such as lever arms, and does not attempt to reach an accuracy greater than 10 degrees.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

I claim:

1. An apparatus for measuring limits of a peripheral visual field of an examinee, comprising:

a gaze-fixing mirror including a dot for fixing a gaze of the examinee;

a backing to which the gaze-fixing mirror is attached;

a measuring tool for measuring the limits of the peripheral visual field; and a base to which the backing and the measuring tool are attached, wherein the measuring tool operates to measure the limits of the peripheral visual field when the gaze of the examinee is fixed on the gaze-fixing mirror and the examinee detects a target in the peripheral visual field, wherein the backing includes a stand to which the gaze-fixing mirror is attached and a back which is hinged to the stand and hinged to the base, and the backing operates to position the gaze-fixing mirror within an angular range so that the dot can be viewed simultaneously by the examinee and an examiner positioned behind the examinee.

2. An apparatus according to claim 1, wherein the backing operates to collapse so that the apparatus is easily transportable by a single hand, and the base includes a storage space for at least one target object that can be used as a target to measure the limits of the peripheral visual field.

3. An apparatus according to claim 2, wherein the gaze-fixing mirror is 2–8 cm in diameter.

4. An apparatus according to claim 2, wherein the measuring tool is attached detachably to the base.

5. An apparatus according to claim 2, wherein said at least one target object comprises:

a blinking light; and a switch operating to control the blinking light.

6. An apparatus according to claim 1, wherein the gaze-fixing mirror is 2–8 cm in diameter.

7. An apparatus according to claim 1, wherein the measuring tool is attached detachably to the base.

8. An apparatus for measuring limits of a peripheral visual field of an examinee, comprising:

- a gaze-fixing mirror including a dot for fixing a gaze of the examinee;
- a backing to which the gaze-fixing mirror is attached;
- a measuring tool for measuring the limits of the peripheral visual field; and
- a base to which the backing and the measuring tool are attached, wherein
- the measuring tool operates to measure the limits of the peripheral visual field when the gaze of the examinee is fixed on the gaze-fixing mirror, a target object is introduced into the peripheral visual field, and the examinee detects the target object,
- the backing includes
  - a stand to which the gaze-fixing mirror is attached and
  - a back which is hinged to the stand and hinged to the base,
- the backing operates to position the gaze-fixing mirror within an angular range so that the dot can be viewed simultaneously by the examinee and an examiner positioned behind the examinee,
- the backing operates to collapse so that the apparatus is easily transportable by a single hand, and
- the base includes a storage space for at least one target object that can be used as a target to measure the limits of the peripheral visual field.

9. An apparatus according to claim 8, wherein the gaze-fixing mirror is 2–8 cm in diameter.

10. An apparatus according to claim 8, wherein the measuring tool is attached detachably to the base.

11. An apparatus according to claim 8, wherein said at least one target object comprises:

blinking light; and a switch operating to control the blinking light.

* * * * *